US010775495B2

(12) United States Patent
Kimura

(10) Patent No.: US 10,775,495 B2
(45) Date of Patent: Sep. 15, 2020

(54) GROUND CONTROL POINT DEVICE AND SAR GEODETIC SYSTEM

(71) Applicant: NEC Corporation, Minato-ku, Tokyo (JP)

(72) Inventor: Tsunekazu Kimura, Tokyo (JP)

(73) Assignee: NEC CORPORATION, Tokyo (JP)

( * ) Notice: Subject to any disclaimer, the term of this patent is extended or adjusted under 35 U.S.C. 154(b) by 345 days.

(21) Appl. No.: 15/944,886

(22) Filed: Apr. 4, 2018

(65) Prior Publication Data
US 2018/0292527 A1 Oct. 11, 2018

(30) Foreign Application Priority Data
Apr. 6, 2017 (JP) .................. 2017-075733

(51) Int. Cl.
| | |
|---|---|
| *G01S 13/90* | (2006.01) |
| *G01N 33/24* | (2006.01) |
| *G01S 19/14* | (2010.01) |
| *G01S 19/02* | (2010.01) |
| *G01S 7/00* | (2006.01) |
| *G01S 7/40* | (2006.01) |
| *G01S 19/42* | (2010.01) |

(52) U.S. Cl.
CPC ............ *G01S 13/90* (2013.01); *G01N 33/246* (2013.01); *G01S 7/003* (2013.01); *G01S 7/4052* (2013.01); *G01S 19/02* (2013.01); *G01S 19/14* (2013.01); *G01S 19/42* (2013.01); *G01S 2007/4091* (2013.01)

(58) Field of Classification Search
CPC .......... G01S 13/90; G01S 19/02; G01N 33/26
See application file for complete search history.

(56) References Cited

U.S. PATENT DOCUMENTS

| | | | |
|---|---|---|---|
| 8,369,622 B1* | 2/2013 | Hsu ...................... | G06K 9/3233 382/181 |
| 2004/0140815 A1* | 7/2004 | Bell ....................... | G01V 11/00 324/644 |
| 2014/0191894 A1* | 7/2014 | Chen ....................... | G01S 13/86 342/52 |
| 2015/0371431 A1* | 12/2015 | Korb ................... | G06K 9/00208 382/113 |
| 2016/0259044 A1* | 9/2016 | Chen ....................... | G01S 13/90 |

(Continued)

FOREIGN PATENT DOCUMENTS

| | | |
|---|---|---|
| JP | 2001-091649 A | 4/2001 |
| JP | 2007-110682 A | 4/2007 |

*Primary Examiner* — Peter M Bythrow

(57) ABSTRACT

A ground control point device 100 is set up at a control point of a Synthetic Aperture Radar (SAR) geodetic system in which SAR analysis. The ground control point device 100 comprises an SAR microwave reflector 10 configured to reflect an SAR microwave incident from an SAR toward an incident direction, a Global Navigation Satellite System (GNSS) receiver 20 configured to receive a GNSS wave to generate, based on the GNSS wave, positional information, which indicates a position of the control point, a ground state detector 30 configured to detect a state of a ground under the control point, the state including at least a moisture content rate of the ground, and a control point data transmitter 40 configured to transmit, to outside, control point data, which includes the positional information and a detection value of the ground state detector 30.

20 Claims, 3 Drawing Sheets

(56) References Cited

U.S. PATENT DOCUMENTS

| | | | |
|---|---|---|---|
| 2016/0282463 A1* | 9/2016 | Guy | G01S 13/885 |
| 2018/0095156 A1* | 4/2018 | Katz | G01S 19/252 |
| 2019/0025423 A1* | 1/2019 | Sajwaj | G01S 13/867 |

* cited by examiner

CONTROL POINT DATA SET AT EACH CONTROL POINT

POSITIONAL INFORMATION PROVIDED BY GNSS ABOUT CONTROL POINT

INFORMATION (E.G., MOISTURE CONTENT RATE) ABOUT GROUND UNDER CONTROL POINT

FIG. 3

GROUND CONTROL POINT DEVICE AND SAR GEODETIC SYSTEM

This application is based upon and claims the benefit of priority from Japanese patent application No. 2017-075733, filed on Apr. 6, 2017, the disclosure of which is incorporated herein in its entirety by reference.

BACKGROUND OF THE INVENTION

Field of the Invention

This invention relates to a ground control point device and an SAR geodetic system.

Description of the Related Art

Known examples of geodetic systems using an artificial satellite or other flying objects include Global Navigation Satellite Systems (GNSSs) such as Global Positioning Systems (GPSs), and Synthetic Aperture Radar (SAR) geodetic systems in which SAR analysis, for example, Persistent Scatterer Interferometry Synthetic Aperture Radar (PS-InSAR) analysis, is conducted.

Some SAR geodetic systems use a ground control point device, which includes, for example, a corner reflector (CR) to reflect a microwave (SAR microwave) transmitted from a flying object toward an incident direction, when it is difficult to use a natural geographical feature, a building, or the like as a ground control point. A SAR geodetic system and a GNSS may be used in combination in order to obtain the absolute position of a ground control point in terms of longitude, latitude, altitude, or other measures.

Technologies related to a geodetic system that uses a flying object are disclosed in, for example, Japanese Unexamined Patent Application Publication JP 2001-091649 A and Japanese Unexamined Patent Application Publication JP 2007-110682 A.

A ground control point device applied to an SAR geodetic system is disclosed in Japanese Unexamined Patent Application Publication JP 2001-091649 A. In Japanese Unexamined Patent Application Publication JP 2001-091649 A, there is disclosed an automobile in which a CR or a similar passive reflective unit and a GPS receiver as a geodetic unit are provided in combination as a ground control point device.

A wireless communication device is also disclosed in Japanese Unexamined Patent Application Publication JP 2007-110682 A, which has a function of obtaining the moisture content rate of the ground and other types of information in addition to positional information. The wireless communication device is not a ground control point device for a geodetic system, but has a GPS receiver as a positional information obtaining unit. The wireless communication device is in the form of a portable terminal, and adopts a method in which information other than positional information, for example, the moisture content rate of the ground, is input from an external measuring instrument.

An example of information that can be obtained with SAR geodetic systems of this type, including the one disclosed in Japanese Unexamined Patent Application Publication JP 2001-091649 A, is information indicating ground movement. The information indicating ground movement is useful for, for example, an evaluation on the stableness of the ground or on the possibility (risk) of disruption/collapse of the ground. A high degree of certainty is preferred in an evaluation on the stableness of the ground or on the risk of disruption/collapse of the ground. An improvement of the degree of certainty is therefore demanded in an evaluation on the stableness of the ground or on the risk of disruption/collapse of the ground. It is conceivable that the degree of certainty in an evaluation on the stableness of the ground or on the risk of disruption/collapse of the ground can be improved when the moisture content rate of the ground and other types of information are available in addition to information indicating ground movement.

SUMMARY OF THE INVENTION

It is an object of this invention to provide a technology for solving the problem described above, by providing a ground control point device that contributes to improvement in the degree of certainty in an evaluation on the stableness of the ground or on the risk of disruption/collapse of the ground.

According to one aspect of this invention, there is provided a ground control point device, which is set up at a control point of a Synthetic Aperture Radar (SAR) geodetic system in which SAR analysis is conducted, the ground control point device comprising an SAR microwave reflector configured to reflect an SAR microwave incident from an SAR toward an incident direction, a Global Navigation Satellite System (GNSS) receiver configured to receive a GNSS wave to generate, based on the GNSS wave, positional information, which indicates a position of the control point, a ground state detector configured to detect a state of a ground under the control point, the state including at least a moisture content rate of the ground, and a control point data transmitter configured to transmit, to outside, control point data, which includes the positional information and a detection value of the ground state detector.

According to another aspect of this invention, there is provided an SAR geodetic system, comprising an SAR provided in a flying object, the ground control point device, and a ground-based station, in which the ground-based station includes a geodetic information processor configured to calculate at least one of: stableness of a ground; and a risk of disruption or collapse of the ground, based on pre-SAR analysis data or post-SAR analysis data from the SAR and on the control point data from the ground control point device.

BRIEF DESCRIPTION OF THE DRAWINGS

The above features and advantages of the present invention will be more apparent from the following description of certain preferred embodiments provided in conjunction with the accompanying drawings, among which:

FIG. 3 is a diagram of the specifics of control point data (a control point data set).

DESCRIPTION OF THE EMBODIMENTS

A ground control point device according to an embodiment of this invention is a ground control point device set up at a control point of a Synthetic Aperture Radar (SAR) geodetic system in which SAR analysis is conducted, and includes an SAR microwave reflector, a GNSS receiver, a ground state detector, and a control point data transmitter.

The SAR microwave reflector reflects an SAR microwave, which is a microwave incident from an SAR, toward the incident direction. The Global Navigation Satellite System (GNSS) receiver receives a GNSS wave and generates, based on the GNSS wave, positional information indicating the position of a control point. The ground state detector detects the state of the ground under a control point, which includes at least the moisture content rate of the ground. The control point data transmitter transmits control point data, which includes the positional information and a detection value of the ground state detector, to the outside.

With the configuration described above, the ground control point device according to this invention contributes to improvement in the degree of certainty in an evaluation on the stableness of the ground or on the risk of disruption/collapse of the ground.

A more specific mode of the ground control point device according to this invention is described below with reference to the drawings.

Figure 1:
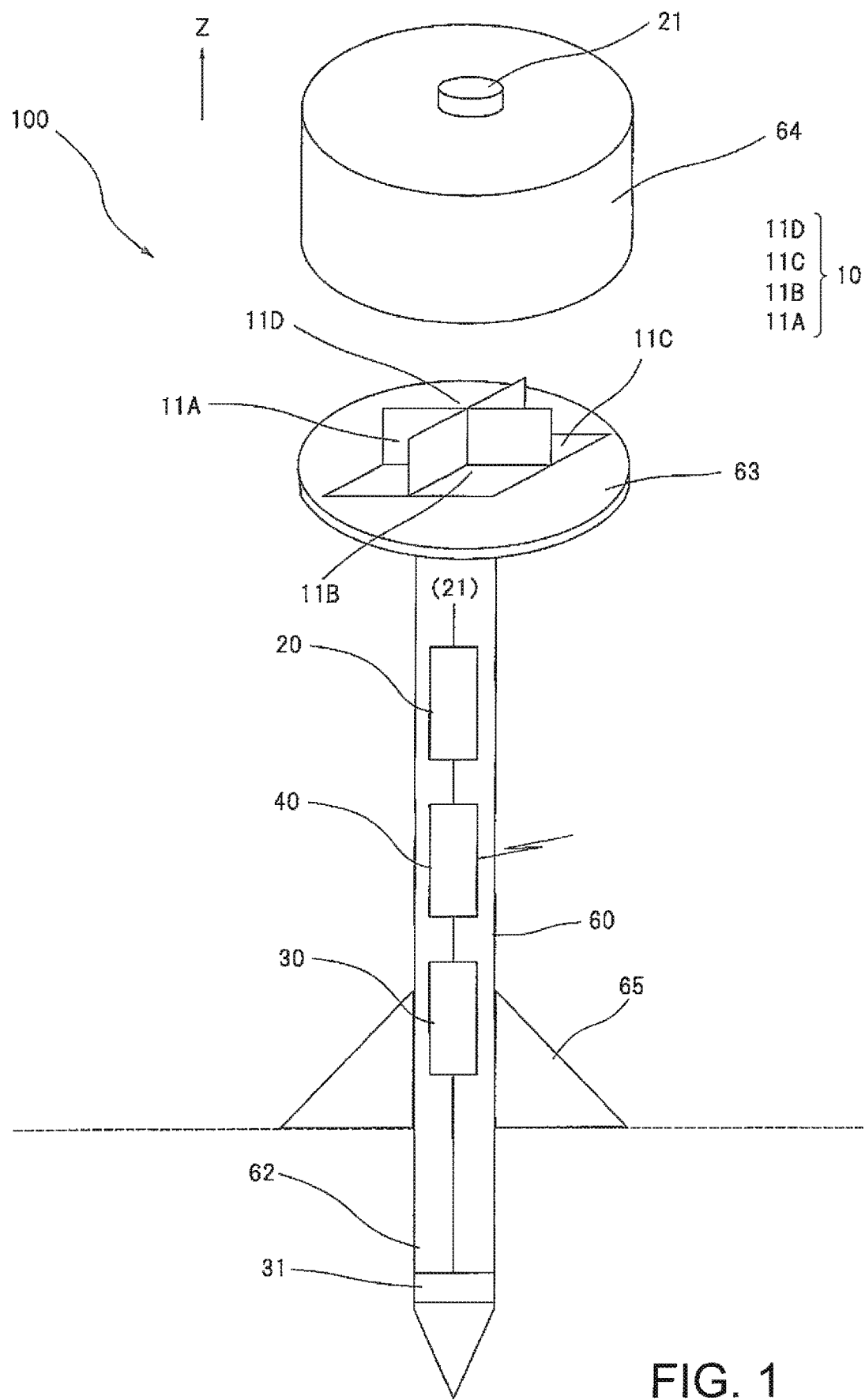
FIG. 1 is a diagram of the configuration of a ground control point device according to an embodiment of this invention.

Referring to FIG. 1, a ground control point device 100 according to the embodiment of this invention is a ground control point device set up at a control point of a Synthetic Aperture Radar (SAR) geodetic system in which SAR analysis is conducted, and includes an SAR microwave reflector 10, a GNSS receiver 20, a ground state detector 30, a control point data transmitter 40, and a housing 60.

The SAR microwave reflector 10 reflects an SAR microwave incident from an SAR toward the incident direction.

The Global Navigation Satellite System (GNSS) receiver 20 receives a GNSS wave and generates, based on the GNSS wave, positional information indicating the position of a control point.

The ground state detector 30 detects the state of the ground under a control point, which includes at least the moisture content rate of the ground. A ground state detector in this invention may detect, other than the moisture content rate of the ground under a control point, the vibration of the ground under a control point with the use of a piezoelectric element, a microphone, or the like, the temperature of the ground under a control point with the use of a temperature sensor, and other states of the ground.

The control point data transmitter 40 transmits control point data, which includes the positional information and a detection value of the ground state detector 30, through wired communication or wireless communication to a host device, in this example, a ground-based station described later.

FIG. 3 is a diagram for illustrating an example of control point data. As illustrated in FIG. 3, control point data (a control point data set) transmitted from the control point data transmitter 40 and unique to each ground control point device 100 includes the positional information provided by the GNSS receiver 20 about a control point, and detection data of the ground state detector 30, namely, the moisture content rate of the ground under a control point and other pieces of information indicating the state of the ground.

The control point data may have the data form of mapping data in which the moisture content rate of the ground under a control point and other pieces of information indicating the state of the ground are plotted at a point on a map based on the positional information provided by the GNSS receiver 20 about the control point. Through transmission of the control point data in the form of mapping data from the control point data transmitter 40 in this manner, a geodetic information processor of the ground-based station described later can efficiently superpose the control point data in the form of mapping data obtained from plural (at least three) ground control point devices and pre-SAR analysis data or post-SAR analysis data received from the SAR, and can accordingly give information useful for the analysis of the result of geodetic information processing. Further, the GNSS receiver 20 is capable of obtaining time information, and control point data in the form of a table in which pieces of control point data that includes information indicating the state of the ground are sorted in time series based on the time of detection by the ground state detector 30 may be transmitted from the control point data transmitter 40.

The housing 60 has a tubular shape or other shapes easy to insert and fix to the ground. A tubular or otherwise shaped main body of the housing 60 houses the GNSS receiver 20, the ground state detector 30, and the control point data transmitter 40. A ground insertion portion 62, which is inserted into the ground, is included on the bottom side of the housing 60 in a top-bottom direction along a zenith direction Z of the housing 60. A reflector support portion 63, which supports the SAR microwave reflector 10, is included on the top side of the housing 60 in the top-bottom direction. A support leg of the ground control point device 100 is denoted by a reference symbol 65 in FIG. 1.

The SAR microwave reflector 10 includes a plurality of corner reflectors, in this example, four corner reflectors 11A to 11D. The four corner reflectors 11A to 11D are arranged about a vertical line extending in the zenith direction Z equiangularly from one another, in this example, at 90° intervals, and are each open to the zenith and to the sides. This enables the SAR microwave reflector 10 to return any SAR microwave, irrespective of from which direction of a hemisphere having its center at the zenith the SAR microwave arrives, toward the incident direction, that is, to return a reflected wave to the SAR. Accordingly, the ground control point device 100 only needs to be set up so that the top-bottom direction of the ground control point device 100 extends along the zenith direction Z to eliminate the need to direct a rotation direction about the zenith direction Z to a particular direction, which means that the ground control point device 100 can be set up with excellent workability. This also eliminates the need for a mechanism that drives the SAR microwave reflector 10 in a panning direction and a tilting direction to suit the position of an SAR artificial satellite, which means that the manufacturing cost is low.

The ground state detector 30 includes a ground sensor 31, which detects at least the moisture content rate of the ground. The ground sensor (moisture content rate sensor) 31 is provided in the ground insertion portion 62 of the housing 60, and is buried in the ground under a control point at a given depth.

The ground control point device 100 also includes a power source (not shown), which supplies power to the GNSS receiver 20, the ground state detector 30, and the control point data transmitter 40. The power source can be a commercial power source or a battery. When the ground control point device 100 is set up in a remote, underdeveloped area or other places in which it is difficult to secure a commercial power source or to maintain a battery, in particular, the ground control point device 100 is designed so that power consumption of the GNSS receiver 20, the ground state detector 30, and the control point data transmitter 40 is as small as possible, and may employ a combination of a private power generator, for example, a solar battery, a geothermal power generation element, or a wind power generator, and a rechargeable battery as the power source.

The ground control point device 100 further includes a radome 64. A surface of the radome 64 is treated with stain-proofing treatment. The radome 64 is made of a material transmissive of SAR microwaves, and covers a top portion and side portion of the SAR microwave reflector 10 to prevent the staining or oxidization of surfaces of the corner reflectors 11A to 11D, and the resultant drop in reflection efficiency with which an SAR microwave is reflected. The GNSS receiver 20 includes a GNSS antenna 21 provided on top of the radome 64 in a place with less chance of hindering the SAR microwave reflection effect of the SAR microwave reflector 10. The GNSS antenna 21 receives GNSS waves from as many GNSS artificial satellites (not shown) as necessary, and outputs a reception signal to the GNSS receiver 20. Wiring connecting the GNSS receiver 20 and the GNSS antenna 21 is omitted from FIG. 1.

Figure 2:
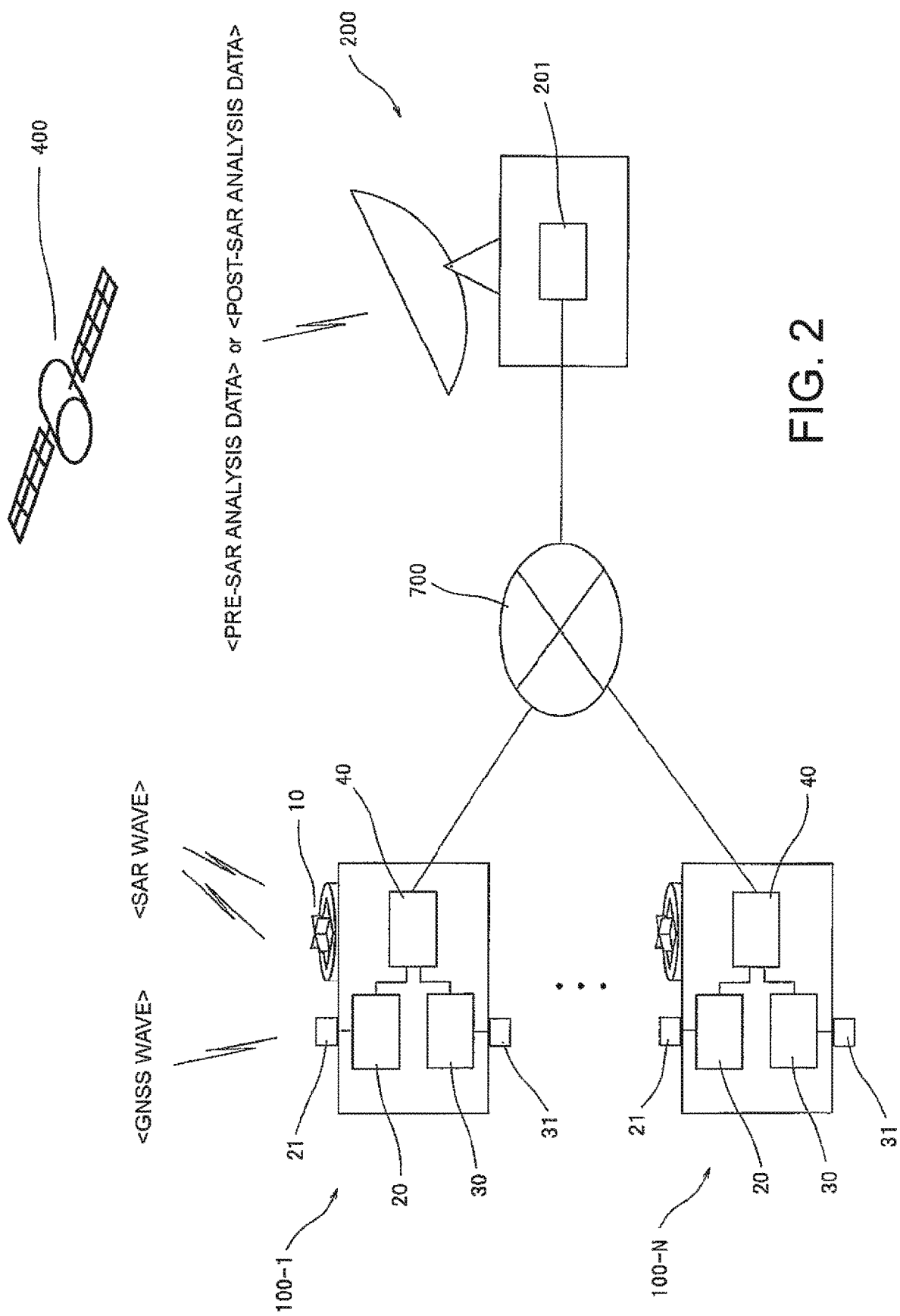
FIG. 2 is a diagram of the configuration of an SAR geodetic system according to the embodiment of this invention.

Referring also to FIG. 2, the SAR geodetic system according to the embodiment of this invention includes an SAR artificial satellite 400, a ground-based station 200, as many GNSS artificial satellites (not shown) as necessary, ground control point devices 100-1 to 100-N (N is a natural number), and a network 700. The SAR artificial satellite 400 includes, at least, an SAR and a communicator for communication to and from the ground-based station described later. The ground control point devices 100-1 to 100-N are provided in necessary places on the ground as indicators of control points for SAR analysis.

The ground-based station 200 includes a geodetic information processor 201. The geodetic information processor 201 calculates at least one of the stableness of the ground under and around a control point and the risk of disruption/collapse of the ground, based on pre-SAR analysis data or post-SAR analysis data received from the SAR of the SAR artificial satellite 400 and on the control point data obtained from the ground control point devices 100-1 to 100-N over the network 700.

What is claimed is:

1. A ground control point device, which is set up at a control point of a Synthetic Aperture Radar (SAR) geodetic system in which SAR analysis is conducted, the ground control point device comprising:
    an SAR microwave reflector configured to reflect an SAR microwave incident from an SAR toward an incident direction;
    a Global Navigation Satellite System (GNSS) receiver configured to receive a GNSS wave to generate, based on the GNSS wave, positional information, which indicates a position of the control point;
    a ground state detector configured to detect a state of a ground under the control point, the state including at least a moisture content rate of the ground; and
    a control point data transmitter configured to transmit, to outside, control point data, which includes the positional information and a detection value of the ground state detector.

2. The ground control point device according to claim 1, wherein the ground state detector includes a ground sensor, which is buried in the ground under the control point, and which is configured to detect at least the moisture content rate of the ground.

3. The ground control point device according to claim 1, wherein the SAR microwave reflector includes a plurality of corner reflectors, and
    wherein the plurality of corner reflectors are arranged about a vertical line extending toward a zenith, equiangularly from one another, and are each open to the zenith and to sides.

4. The ground control point device according to claim 2, wherein the SAR microwave reflector includes a plurality of corner reflectors, and
    wherein the plurality of corner reflectors are arranged about a vertical line extending toward a zenith, equiangularly from one another, and are each open to the zenith and to sides.

5. The ground control point device according to claim 1, further comprising a housing, which has a tubular shape, wherein the housing includes:
    a ground insertion portion, which is provided on a bottom side of the housing to be inserted into the ground; and
    a reflector support portion, which is provided on a top side of the housing to support the SAR microwave reflector.

6. The ground control point device according to claim 2, further comprising a housing, which has a tubular shape, wherein the housing includes:
    a ground insertion portion, which is provided on a bottom side of the housing to be inserted into the ground; and
    a reflector support portion, which is provided on a top side of the housing to support the SAR microwave reflector.

7. The ground control point device according to claim 4, further comprising a housing, which has a tubular shape, wherein the housing includes:
    a ground insertion portion, which is provided on a bottom side of the housing to be inserted into the ground; and
    a reflector support portion, which is provided on a top side of the housing to support the SAR microwave reflector.

8. The ground control point device according to claim 6, wherein the ground insertion portion of the housing is provided with the ground sensor.

9. The ground control point device according to claim 7, wherein the ground insertion portion of the housing is provided with the ground sensor.

10. The ground control point device according to claim 1, further comprising a radome, which is made of a material transmissive of SAR microwaves, and which is configured to cover a top portion and side portion of the SAR microwave reflector,
    wherein the GNSS receiver includes a GNSS antenna, which is provided on top of the radome to receive a GNSS wave.

11. The ground control point device according to claim 2, further comprising a radome, which is made of a material transmissive of SAR microwaves, and which is configured to cover a top portion and side portion of the SAR microwave reflector,
    wherein the GNSS receiver includes a GNSS antenna, which is provided on top of the radome to receive a GNSS wave.

12. The ground control point device according to claim 3, further comprising a radome, which is made of a material transmissive of SAR microwaves, and which is configured to cover a top portion and side portion of the SAR microwave reflector,
    wherein the GNSS receiver includes a GNSS antenna, which is provided on top of the radome to receive a GNSS wave.

13. The ground control point device according to claim 4, further comprising a radome, which is made of a material transmissive of SAR microwaves, and which is configured to cover a top portion and side portion of the SAR microwave reflector, wherein the GNSS receiver includes a GNSS antenna, which is provided on top of the radome to receive a GNSS wave.

14. The ground control point device according to claim 5, further comprising a radome, which is made of a material transmissive of SAR microwaves, and which is configured to cover a top portion and side portion of the SAR microwave reflector, wherein the GNSS receiver includes a GNSS antenna, which is provided on top of the radome to receive a GNSS wave.

15. The ground control point device according to claim 6, further comprising a radome, which is made of a material transmissive of SAR microwaves, and which is configured to cover a top portion and side portion of the SAR microwave reflector, wherein the GNSS receiver includes a GNSS antenna, which is provided on top of the radome to receive a GNSS wave.

16. The ground control point device according to claim 7, further comprising a radome, which is made of a material transmissive of SAR microwaves, and which is configured to cover a top portion and side portion of the SAR microwave reflector, wherein the GNSS receiver includes a GNSS antenna, which is provided on top of the radome to receive a GNSS wave.

17. The ground control point device according to claim 8, further comprising a radome, which is made of a material transmissive of SAR microwaves, and which is configured to cover a top portion and side portion of the SAR microwave reflector, wherein the GNSS receiver includes a GNSS antenna, which is provided on top of the radome to receive a GNSS wave.

18. The ground control point device according to claim 9, further comprising a radome, which is made of a material transmissive of SAR microwaves, and which is configured to cover a top portion and side portion of the SAR microwave reflector, wherein the GNSS receiver includes a GNSS antenna, which is provided on top of the radome to receive a GNSS wave.

19. The ground control point device according to claim 1, wherein the ground state detector is configured to detect at least one of a vibration of the ground and a temperature of the ground as the state of the ground under the control point, in addition to the moisture content rate of the ground.

20. An SAR geodetic system, comprising:

an SAR provided in a flying object;

the ground control point device of claim 1; and a ground-based station, wherein the ground-based station includes a geodetic information processor configured to calculate at least one of: stableness of a ground; and a risk of disruption or collapse of the ground, based on pre-SAR analysis data or post-SAR analysis data from the SAR and on the control point data from the ground control point device.

* * * * *